United States Patent [19]

Cantatore et al.

[11] Patent Number: 5,026,749
[45] Date of Patent: Jun. 25, 1991

[54] PIPERIDINE COMPOUNDS FOR USE AS LIGHT STABILIZERS, HEAT STABILIZERS AND OXIDATION STABILIZERS FOR ORGANIC MATERIAL

[75] Inventors: Giuseppe Cantatore, Bitonto; Valerio Borzatta, Bologna; Franca Masina, Anzola Emilia, all of Italy

[73] Assignee: Ciba-Geigy Corporation, Ardsley, N.Y.

[21] Appl. No.: 523,288

[22] Filed: May 14, 1990

Related U.S. Application Data

[63] Continuation of Ser. No. 393,034, Aug. 10, 1989, abandoned, which is a continuation of Ser. No. 187,174, Apr. 28, 1988, abandoned.

[30] Foreign Application Priority Data

May 7, 1987 [IT] Italy ............................... 20419 A/87

[51] Int. Cl.$^5$ .................. C08K 5/3435; C07D 211/58
[52] U.S. Cl. ...................................... 524/99; 524/100; 524/102; 524/103; 546/186; 546/190; 546/223; 546/224
[58] Field of Search .................. 524/99, 100, 102, 103; 546/186, 190, 223, 224

[56] References Cited

U.S. PATENT DOCUMENTS

| 4,500,662 | 2/1985 | Lai | 524/99 |
|---|---|---|---|
| 4,578,454 | 3/1986 | Cantatore | 528/327 |
| 4,618,634 | 10/1986 | Cantatore et al. | 524/97 |

FOREIGN PATENT DOCUMENTS

| 0172413 | 2/1986 | European Pat. Off. |
| 62-63570 | 3/1987 | Japan |
| 1318559 | 5/1973 | United Kingdom |
| 1401924 | 8/1975 | United Kingdom |

OTHER PUBLICATIONS

Chem. Abst. 91, 92571s (1979).
Derwent 17983c/10 = Russian 670,588.

Primary Examiner—Kriellion Morgan
Attorney, Agent, or Firm—Luther A. R. Hall

[57] ABSTRACT

The novel compounds of the formula (I)

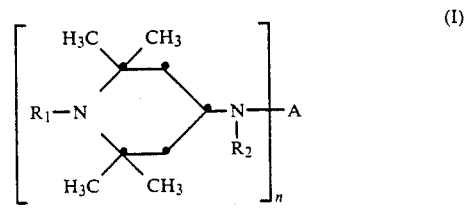

in which n is 1 or 2, $R_1$ is hydrogen, O·, OH, NO, $CH_2CN$, $C_1$–$C_8$-alkyl, allyl, benzyl, hydroxyalkyl, alkoxy, cycloalkoxy or acyl, $R_2$ is alkyl, cycloalkyl, phenylalkyl, alkoxyalkyl, tetrahydrofurfuryl or a group of the formula (II)

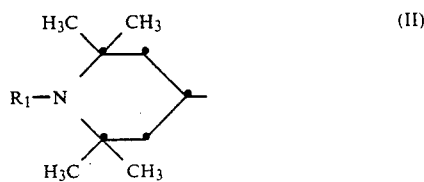

and A is a monovalent or divalent moiety, in which $R_1$ is as defined above, and, if $n=1$, A is a group of the formula (III) in which each $R_9$ independently is hydrogen or methyl, r is zero or 1 and are useful as light stabilizers, heat stabilizers and oxidation stabilizers for organic materials.

15 Claims, No Drawings

PIPERIDINE COMPOUNDS FOR USE AS LIGHT STABILIZERS, HEAT STABILIZERS AND OXIDATION STABILIZERS FOR ORGANIC MATERIAL

This is a continuation of application Ser. No. 393,034, filed on Aug. 10, 1989, now abandoned, which in turn is a continuation of application Ser. No. 187,174, filed on Apr. 28, 1988, now abandoned.

The present invention relates to novel piperidine compounds, the use thereof as light stabilizers, heat stabilizers and oxidation stabilizers as well as to the stabilized organic materials.

It is known that synthetic polymers undergo progressive changes in their physical properties, such as loss of mechanical strength and colour changes, when they are exposed to sunlight or other sources of ultraviolet light.

To retard the deleterious effect of ultraviolet radiation on synthetic polymers, it has been proposed to use various additives having light-stabilizing properties, such as certain derivatives of benzophenone and benzotriazole, nickel complexes, substituted benzoic acid esters, alkylidenemalonates, cyanoacrylates, aromatic oxamides and sterically hindered amines.

British Patent Nos. 1,318,559 and 1,401,924 claim polymeric compositions stabilized with 4-amino-piperidine derivatives. Soviet Patent No. 670,588 and European Patent No. 172,413 relate to 4-(piperidylaminoalkylamido)piperidines and the use thereof as stabilizers. U.S. Pat. No. 4,500,662 describes polysubstituted α-aminoacetamides. Japanese Patent Laid Open Print No. 87-63570 claims piperidylamino acid derivatives which are useful as stabilizers for polymeric materials.

In particular, the present invention relates to novel compounds of the general formula (I)

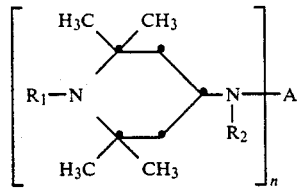
(I)

in which n is 1 or 2, $R_1$ is hydrogen, O·, OH, NO, $CH_2CN$, $C_1$–$C_8$-alkyl, allyl, benzyl, OH-monosubstituted $C_2$–$C_4$-alkyl, $C_1$–$C_{18}$-alkyloxy, $C_5$–$C_{12}$-cycloalkyloxy or $C_1$–$C_8$-acyl, $R_2$ is $C_1$–$C_{18}$-alkyl, $C_5$–$C_{12}$-cycloalkyl, $C_7$–$C_{12}$-phenylalkyl, $C_1$–$C_{12}$-alkoxy-monosubstituted $C_2$–$C_4$-alkyl, tetrahydrofurfuryl or a group of the formula (II)

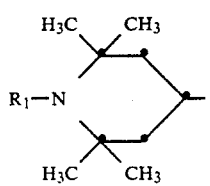
(II)

in which $R_1$ is as defined above, and, if n=1, A is a group of the formula (III)

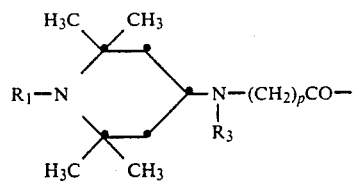
(III)

in which $R_1$ is as defined above, $R_3$ is as defined for $R_2$ and p is an integer from 1 to 5, or, if n=2, A is a group of the formula (IV), (V), (VI) or (VII)

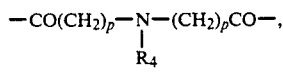
(IV)

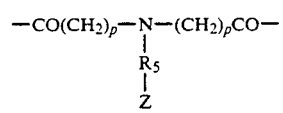
(V)

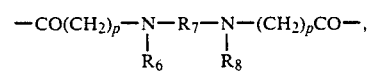
(VI)

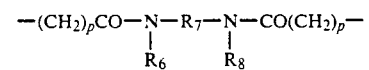
(VII)

in which p is as defined above, $R_4$ is as defined above for $R_2$, $R_5$ is $C_2$–$C_{12}$-alkylene, $C_6$–$C_{15}$-cycloalkylene or xylylene, Z is a group of the formula (VIII)

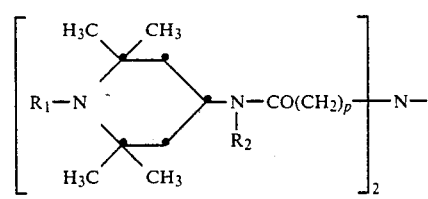
(VIII)

in which $R_1$, $R_2$ and p are as defined above, $R_6$ and $R_8$ which can be identical or different are $C_1$–$C_8$-alkyl, cyclohexyl, benzyl or a group of the formula (II) and $R_7$ is $C_2$–$C_{12}$-alkylene, $C_6$–$C_{15}$-cycloalkylene or xylylene, or the group

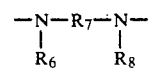

is a heterocyclic radical of the formula (IX) or (X)

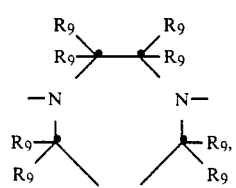
(IX)

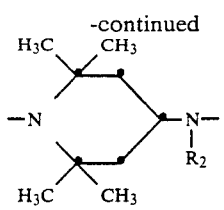 (X)

in which each $R_9$ independently is hydrogen or methyl, r is zero or 1 and $R_2$ is as defined above.

Representative examples of $R_1$, $R_6$ and $R_8$ as $C_1$–$C_8$-alkyl are methyl, ethyl, propyl, isopropyl, butyl, isobutyl, pentyl, hexyl, heptyl and octyl. $C_1$–$C_4$-alkyl is preferred. $R_1$ as methyl is especially preferred.

Representatives of $R_1$ as $C_2$–$C_4$-alkyl monosubstituted by OH, preferably in the 2, 3 or 4 position, are 2-hydroxyethyl, 2-hydroxypropyl, 3-hydroxypropyl, 2-hydroxybutyl and 4-hydroxybutyl. 2-Hydroxyethyl is preferred.

$R_1$ as $C_1$–$C_8$-acyl may be an aliphatic or aromatic acyl group. $C_1$–$C_8$-alkanoyl, $C_3$–$C_8$-alkenoyl and benzoyl are preferred. Examples are formyl, acetyl, propionyl, butyryl, valeryl, caproyl, capryloyl, benzoyl, acryloyl and crotonoyl. Acetyl is especially preferred.

$R_1$ as $C_1$–$C_{18}$-alkyloxy is for example methoxy, ethoxy, n-propoxy, n-butoxy, sec-butoxy, tert-butoxy, n-hexyloxy, n-octyloxy, 2-ethylhexyloxy, n-nonyloxy, n-decyloxy, n-undecyloxy, n-dodecyloxy, n-tridecyloxy, n-tetradecyloxy, n-hexadecyloxy or n-octadecyloxy. $C_6$–$C_{12}$-alkyloxy, in particular heptyloxy and octyloxy, is preferred.

$R_1$ as $C_5$–$C_{12}$-cycloalkyloxy is for example cyclopentyloxy, cyclohexyloxy, cyclooctyloxy, cyclononyloxy or cyclododecyloxy. Cyclopentyloxy and cyclohexyloxy are preferred.

Representative examples of $R_2$, $R_3$ and $R_4$ as $C_1$–$C_{18}$-alkyl are methyl, ethyl, propyl, isopropyl, butyl, 2-butyl, isobutyl, t-butyl, pentyl, hexyl, heptyl, octyl, 2-ethylhexyl, 1,1,3,3-tetramethylbutyl, nonyl, decyl, undecyl, dodecyl, tridecyl, tetradecyl, hexadecyl and octadecyl. $R_2$ as $C_1$–$C_8$-alkyl and $R_4$ as $C_4$–$C_{12}$-alkyl are preferred.

Representative examples of $R_2$, $R_3$ and $R_4$ as $C_5$–$C_{12}$-cycloalkyl are cyclopentyl, cyclohexyl, methylcyclohexyl, dimethylcyclohexyl, trimethylcyclohexyl, t-butylcyclohexyl, cyclooctyl and cyclododecyl. $R_2$, $R_3$ and $R_4$ as cycloalkyl are preferably a group of the formula

with a being an integer from 4 to 7. Said group may optionally be substituted by $C_1$–$C_4$-alkyl. Cyclohexyl is preferred.

$R_2$, $R_3$ and $R_4$ as $C_7$–$C_{12}$-phenylalkyl are in particular benzyl or 2-phenylethyl, each unsubstituted or substituted at the phenyl ring by $C_1$–$C_4$-alkyl. Representative examples are benzyl, methylbenzyl, dimethylbenzyl, trimethylbenzyl, t-butylbenzyl and 2-phenylethyl. Benzyl is preferred.

$R_2$, $R_3$ and $R_4$ as $C_2$–$C_4$-alkyl monosubstituted by $C_1$–$C_{12}$-alkoxy, preferably in the 2, 3 or 4 position, are for example 2-methoxyethyl, 2-ethoxyethyl, 2-butoxyethyl, 3-methoxypropyl, 3-ethoxypropyl, 3-butoxypropyl, 3-octyloxypropyl, 3-dodecyloxypropyl or 4-methoxybutyl.

Representative examples of $R_5$ and $R_7$ as $C_2$–$C_{12}$-alkylene are ethylene, propylene, trimethylene, tetramethylene, pentamethylene, 2,2-dimethyltrimethylene, hexamethylene, octamethylene, decamethylene and dodecamethylene. $C_2$–$C_6$-alkylene is preferred.

$R_5$ and $R_7$ as $C_6$–$C_{15}$-cycloalkylene may be a saturated hydrocarbon group with two free valencies and at least one cyclic unit, e.g. cyclohexylene, alkylene-cyclohexylene-alkylene with 8 to 15 carbon atoms, cyclohexylene-alkylene-cyclohexylene with 13 to 15 carbon atoms or alkylidenedicyclohexylene with 14 or 15 carbon atoms. Representative examples are cyclohexylene, cyclohexylenedimethylene, methylenedicyclohexylene and isopropylidenedicyclohexylene. Cyclohexylene is preferred.

Illustrative examples of the group

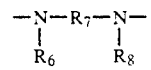

representing a heterocyclic radical are

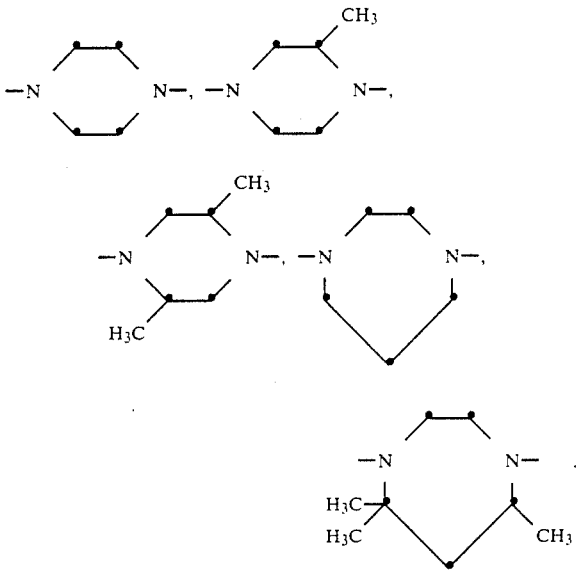

Those compounds of the formula (I) are preferred in which n is 1 or 2, $R_1$ is hydrogen, $CH_2CN$, $C_1$–$C_4$-alkyl, allyl, benzyl, OH-monosubstituted $C_2$–$C_3$-alkyl or acetyl, $R_2$ is $C_1$–$C_{12}$-alkyl, $C_5$–$C_9$-cycloalkyl, benzyl, $C_1$–$C_8$-alkoxy-monosubstituted $C_2$–$C_3$-alkyl, tetrahydrofurfuryl or a group of the formula (II) and, if n=1, A is a group of the formula (III) in which $R_1$ is as defined above, $R_3$ is as defined for $R_2$ and p is an integer from 1 to 3, or, if n=2, A is one of the groups of the formulae (IV), (V), (VI) or (VII) in which p is as defined above, $R_4$ is as defined above for $R_2$, $R_5$ is $C_2$–$C_6$-alkylene or $C_6$–$C_{13}$-cycloalkylene, Z is a group of the formula (VIII) with $R_1$, $R_2$ and p being as defined above, $R_6$ and $R_8$ are a group of the formula (II) and $R_7$ is $C_2$–$C_6$-alkylene or $C_6$–$C_{13}$-cycloalkylene, or the group

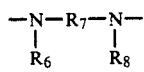

is 1,4-piperazinediyl or 5,5,7-trimethyl-1,4-homopiperazinediyl.

Those compounds of the formula (I) are also preferred in which n is 1 or 2, $R_2$ is $C_1$-$C_{12}$-alkyl, cyclohexyl, benzyl, $C_1$-$C_4$-alkoxy-monosubstituted $C_2$-$C_3$-alkyl or a group of the formula (II) and, if n=1, A is a group of the formula (III) with $R_1$ being as defined above, $R_3$ being as defined for $R_2$ and p being 1 or 2, or, if n=2, A is a group of the formula (IV), (V), (VI) or (VII) in which p is 1 or 2, $R_4$ is as defined above for $R_2$, $R_5$ is $C_2$-$C_6$-alkylene and Z is a group of the formula (VIII) with $R_1$, $R_2$ and p being as defined above, $R_6$ and $R_8$ are a group of the formula (II) and $R_7$ is $C_2$-$C_6$-alkylene, or the group

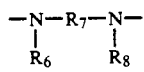

is a group of the formula (X) or 1,4-piperazinediyl.

$R_1$ is in particular hydrogen or methyl.

Those compounds of the formula (I) are especially preferred in which n is 1 or 2, $R_1$ is hydrogen or methyl, $R_2$ is $C_1$-$C_{12}$-alkyl, cyclohexyl, benzyl, $C_1$-$C_4$-alkoxy-monosubstituted $C_2$-$C_3$-alkyl or a group of the formula (II) with $R_1$ being hydrogen or methyl and, if n=1, A is a group of the formula (III) with $R_1$ being hydrogen or methyl, $R_3$ being as defined above for $R_2$ and p being 1 or 2, or, if n=2, A is a group of the formula (IV), (V), (VI) or (VII) in which p is 1 or 2, $R_4$ is as defined above for $R_2$, $R_5$ is $C_2$-$C_6$-alkylene and Z is a group of the formula (VIII) with $R_1$, $R_2$ and p being as defined above, $R_6$ and $R_8$ are 2,2,6,6-tetramethyl-4-piperidyl or 1,2,2,6,6-pentamethyl-4-piperidyl and $R_7$ is $C_2$-$C_6$-alkylene, or the group

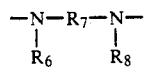

is 1,4-piperazinediyl.

Those compounds of the formula (I) are of particular interest, in which n is 1 or 2, $R_1$ is hydrogen or methyl, $R_2$ is $C_1$-$C_{12}$-alkyl and, if n=1, A is a group of the formula (III) in which $R_1$ is hydrogen or methyl, $R_3$ is $C_1$-$C_{12}$-alkyl and p is 1, or, if n=2, A is a group of the formula (IV), (V) or (VII) in which p is 1, $R_4$ is $C_1$-$C_{12}$-alkyl, cyclohexyl, benzyl, 2,2,6,6-tetramethyl-4-piperidyl or 1,2,2,6,6-pentamethyl-4-piperidyl, $R_5$ is $C_2$-$C_6$-alkylene, Z is a group of the formula (VIII) in which $R_1$ is hydrogen or methyl, $R_2$ is $C_1$-$C_{12}$-alkyl and p is 1, $R_6$ and $R_8$ are 2,2,6,6-tetramethyl-4-piperidyl or 1,2,2,6,6-pentamethyl-4-piperidyl and $R_7$ is $C_2$-$C_6$-alkylene, or the group

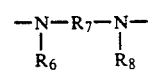

is 1,4-piperazinediyl.

n is preferably 2.

Those compounds of the formula (I) are also of particular interest, in which n is 2, $R_1$ is hydrogen or methyl, $R_2$ is $C_1$-$C_8$-alkyl, A is a group of the formula (IV) or (VII) in which p is 1, $R_4$ is $C_4$-$C_{12}$-alkyl, cyclohexyl, benzyl, 2,2,6,6-tetramethyl-4-piperidyl or 1,2,2,6,6-pentamethyl-4-piperidyl, $R_6$ and $R_8$ are 2,2,6,6-tetramethyl-4-piperidyl or 1,2,2,6,6-pentamethyl-4-piperidyl and $R_7$ is $C_2$-$C_6$-alkylene or the group

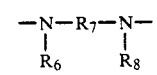

is 1,4-piperazinediyl.

According to a further preferred embodiment n is 2, $R_1$ is hydrogen, $R_2$ is $C_1$-$C_4$-alkyl, A is a group of the formula (IV) or (VII) in which p is 1, $R_4$, $R_6$ and $R_8$ are 2,2,6,6-tetramethyl-4-piperidyl and $R_7$ is $C_2$-$C_6$-alkylene.

Especially preferred examples of compounds of the formula (I) are:

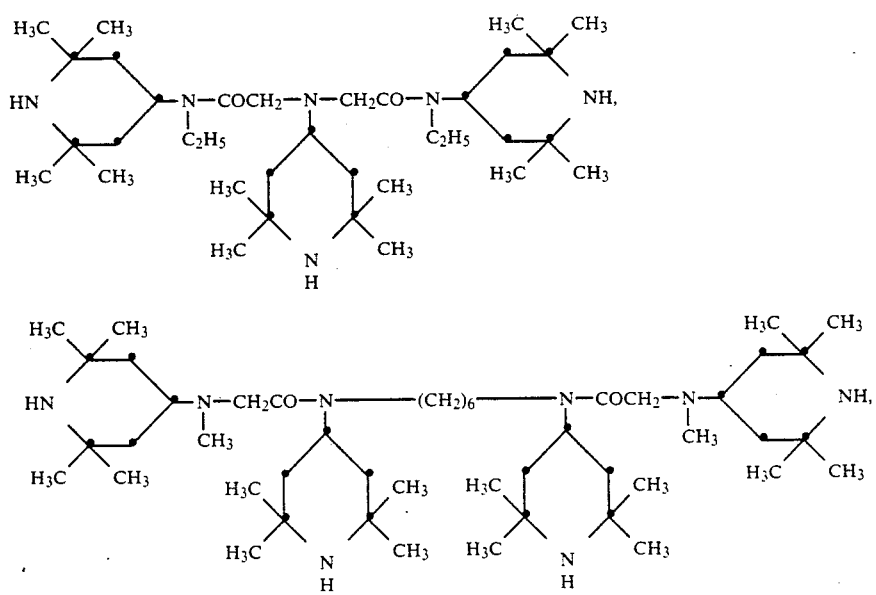

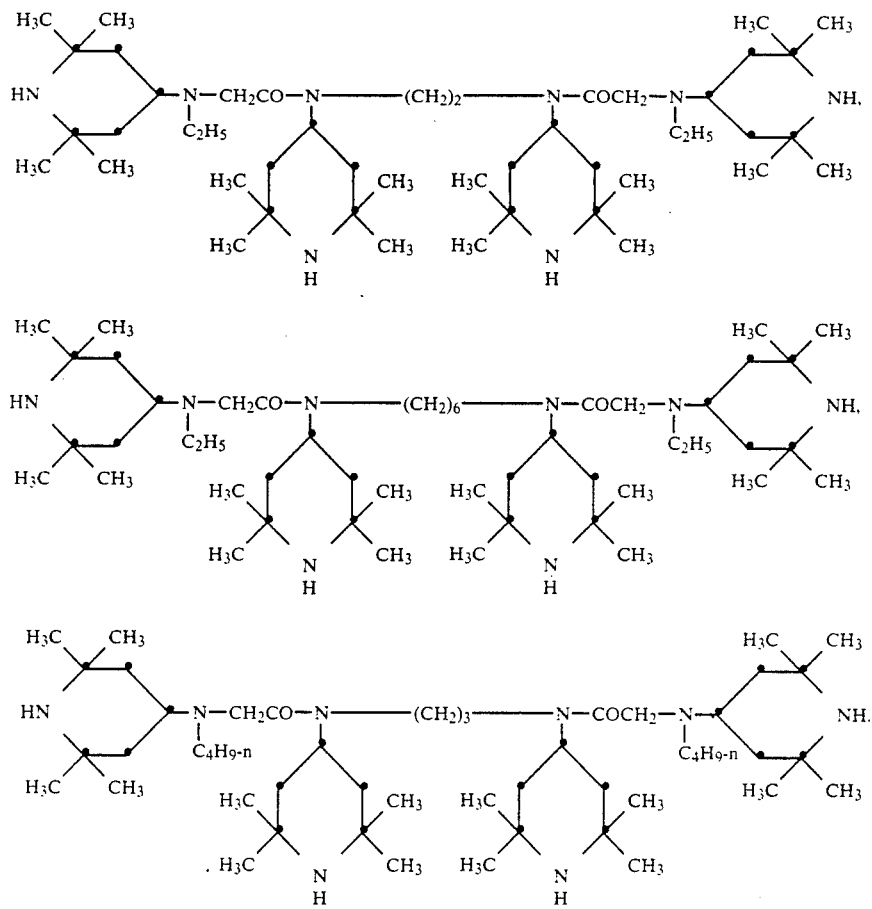

The compounds of the formula (I) can be prepared by analogy to methods known per se, for example, if n=1, by reacting a compound of the formula (XI) with a compound of the formula (XII), the intermediate of the formula (XIII) being formed which is then reacted with a compound of the formula (XIV).

Scheme 1:

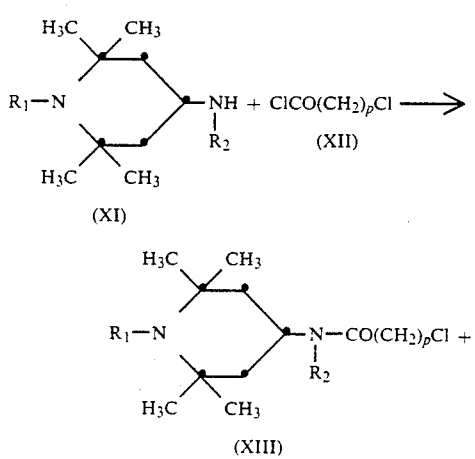

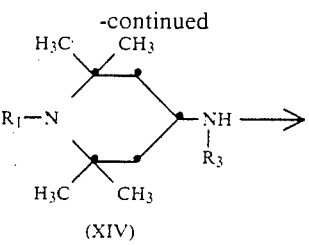

For example, if $R_2=R_3$, the compounds of the formula (XV) can be obtained directly from 2 moles of piperidylamine (XI) and 1 mole of the compound (XII), or, if $R_2=R_3$ and p=1, the compounds of the formula (XV) can be obtained by reacting 2 moles of piperidylamine (XI) with one mole of glyoxal.

If n is 2 and A is a group of the formula (IV), the compounds of the formula (I) can be prepared e.g. according to scheme 2 by reacting 2 moles of a compound of the formula (XIII) with one mole of a compound of the formula (XVI).

Scheme 2:

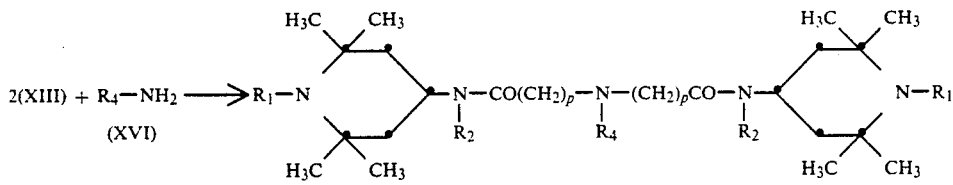

If n is 2 and A is a group of the formula (V), the compounds of the formula (I) can be prepared e.g. according to scheme 3 by reacting 4 moles of a compound of the formula (XIII) with 1 mole of a compound of the formula (XVII).

Scheme 3:

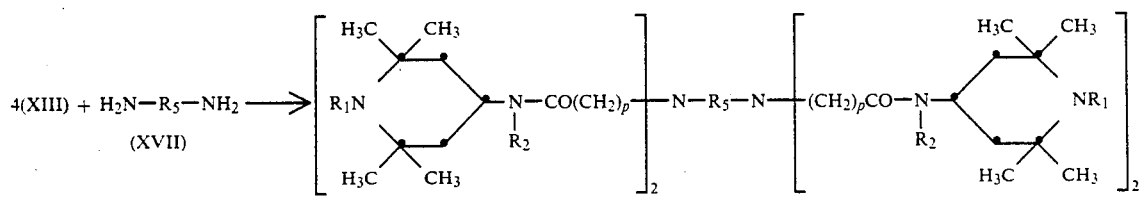

If n is 2 and A is a group of the formula (VI), the compounds of the formula (I) can be prepared e.g. according to scheme 4 by reacting 2 moles of a compound of the formula (XIII) with 1 mole of a compound of the formula (XVIII).

Scheme 4:

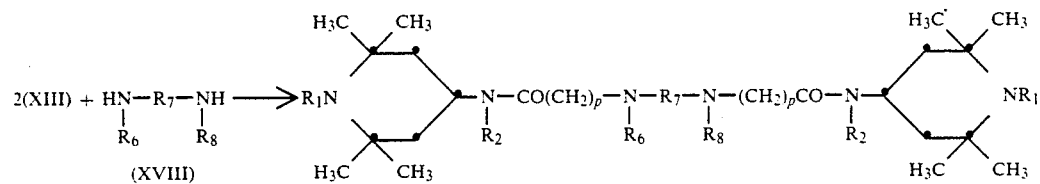

If n is 2 and A is a group of the formula (VII), the compounds of the formula (I) can be prepared e.g. according to scheme 5 by reacting 2 moles of piperidylamine (XI) with 1 mole of a compound of the formula (XIX).

Scheme 5:

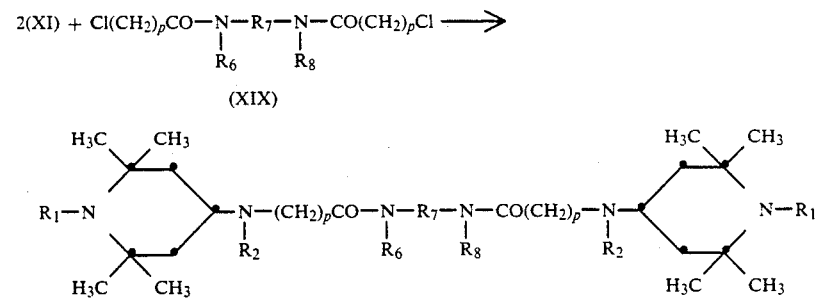

The reactions according to schemes 1–5 can be carried out e.g. in an organic solvent in the presence of an organic or inorganic base at a temperature between 50° and 200° C., preferably between 60° and 150° C. Examples of organic solvents which can be used as the reaction medium are benzene, toluene, xylene, ethylbenzene, trimethylbenzene, decalin, methanol, ethanol, isopropanol, n-butanol, isobutanol, n-pentanol, isopentanol, t-pentanol, 4-methyl-2-pentanol, 2-methoxyethanol, 2-ethoxyethanol, 2-butoxyethanol, tetrahydrofuran, dioxane, dibutyl ether, 1,2-dimethoxyethane, 1,2-diethoxyethane, diethylene glycol dimethyl ether, diethylene glycol diethyl ether, N,N-dimethylformamide, N,N-dimethylacetamide, N-methylpyrrolidone and dimethyl sulfoxide. The preferred bases for neutralizing the hydrochloric acid liberated in the reactions are inorganic bases, in particular the hydroxide or carbonate of sodium or potassium, which are conveniently used in a quantity at least equivalent to the acid.

The ratio of the reagents is preferably theoretical.

The starting materials are known and can be prepared by analogy to known methods, if not commercially available. The chloroamides of the formula (XIII) and (XIX), which are intermediates for preparing the compounds of the formula (I), can be prepared, for example, as described in U.S. Pat. Nos. 4,578,454 and 4,618,634.

As mentioned at the outset, the compounds of the formula (I) are very effective in improving the light stability, heat stability and oxidation stability of organic materials, especially synthetic polymers.

Therefore, a further object of the invention is a composition comprising an organic material subject to thermal, oxidative or light-induced degradation and at least one compound of the formula (I).

Examples of organic materials which can be stabilized are:

1. Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE).

2. Mixtures of the polymers mentioned under (1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefines and diolefines with each other or with other vinyl monomers, such as, for example, ethylene/propylene, linear low density polyethylene (LLDPE) and its mixtures with low density polyethylene (LDPE), propylene/butene-1, ethylene/hexene, ethylene/ethylpentene, ethylene/heptene, ethylene/octene, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene; as well as mixtures of such copolymers and their mixtures with polymers mentioned in (1) above, for example polypropylene/ethylene-propylene-copolymers, LDPE/EVA, LDPE/EAA, LLDPE/EVA and LLDPE/EAA.

3a. Hydrocarbon resins (for example $C_5$–$C_9$) and hydrogenated modifications thereof (for example tackyfiers).

4. Polystyrene, poly-(p-methylstyrene), poly-(α-methylstyrene).

5. Copolymers of styrene or α-methylstyrene with dienes or acrylic derivatives, such as, for example, styrene/butadiene, styrene/acrylonitrile, styrene/alkyl methacrylate, styrene/maleic anhydride, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene or α-methylstyrene such as, for example, styrene on polybutadiene, styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under (8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in (1) above.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as a comonomer; polyacetals modified with thermoplastic polyurethanes, acrylates or MBS.

13. Polyphenylene oxides and sulfides, and mixtures of polyphenylene oxides with polystyrene or polyamides.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained by condensation of m-xylenediamine and adipic acid; polyamides prepared from hexamethylenediamine and isophthalic or/and terephthalic acid and optionally an elastomer as modifier, for example poly-2,4,4,-trimethylhexamethylene terephthalamide or poly-m-phenylene isophthalamide. Further copolymers of the aforementioned polyamides with polyolefins, olefin copolymers, ionomers or chemically bonded or grafted elastomers; or with polyethers, such as for instance, with polyethylene glycols, polypropylene glycols or polytetramethylene glycols. Polyamides or copolyamides modified with EPDM or ABS. Polyamides condensed during processing (RIM-polyamide systems).

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylolcyclohexane terephthalate, poly-[2,2,-(4-hydroxyphenyl)-propane] terephthalate and polyhydroxybenzoates as well as block-copolyetheresters derived from polyethers having hydroxyl end groups.

18. Polycarbonates and polyester-carbonates.

19. Polysulfones, polyether-sulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or polyesteracrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymer-homologous manner, such as cellulose acetates, cellulose propionates and cellulose butyrates, or the cellulose ethers, such as methylcellulose; rosins and their derivatives.

27. Mixtures of polymers as mentioned above, for example PP/EPDM, Polyamide 6/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPE.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellithates) and also mixtures of synthetic esters with mineral oils in any weight ratios, which materials may be used as plasticizer for polymers or as textile spinning oils, as well as aqueous emulsions of such materials.

29. Aqueous emulsions of natural or synthetic rubber, e.g. natural latex or latices of carboxylated styrene/butadiene copolymers.

The compounds of the formula (I) are in particular useful for stabilizing a polyolefine, e.g. polyethylene or polypropylene.

The compounds of the formula (I) can be mixed with the material to be stabilized in various proportions depending on the nature of said material, the end use and the presence of other additives. In general, it is appropriate to use 0.01 to 5% by weight of the compounds of the formula (I), relative to the weight of the polymers, preferably from 0.05 to 1%. The compounds of the formula (I) can be incorporated into the polymeric materials by various processes, such as dry blending in the form of powders, or wet mixing in the form of solutions or suspensions or also in the form of a masterbatch; in these operations, the polymer can be employed in the form of powder, granules, solutions, suspensions or in the form of a latex.

The polymers stabilized with the products of the formula (I) can be used for the preparation of moulded articles, films, tapes, monofilaments, surface-coatings and the like.

If desired, other additives, such as antioxidants, UV absorbers, nickel stabilizers, pigments, fillers, plasticizers, antistatic agents, flameproofing agents, lubricants, corrosion inhibitors and metal deactivators, can be added to the mixtures of the compounds of the formula (I) with the polymeric materials.

Examples of additives which can be mixed with the compounds of the formula (I) are in particular:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol.

1.3. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).

1.4. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl] terephthalate.

1.5. Benzyl compounds, for example 1,3,5-tris(3,5-di-tert-butyl-4-hydroxybenzyl)-2,4,6-trimethylbenzene, bis(3,5-di-tert-butyl-4-hydroxybenzyl) sulfide, isooctyl 3,5-di-tert-butyl-4-hydroxybenzylmercaptoacetate, bis(4-tert-butyl-3-hydroxy-2,6-dimethylbenzyl) dithiolterephthalate, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl)isocyanurate.

1.6. Acylaminophenols, for example lauric acid 4-hydroxyanilide, stearic acid 4-hydroxyanilide, 2,4-bis- (octylmercapto)-6-(3,5-di-tert-butyl-4-hydroxyanilino)-s-triazine, octyl N-(3,5-di-tert-butyl-4-hydroxyphenyl)-carbamate.

1.7. Esters of β-(3,5-di-tert-butyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.8. Esters of β-(5-tert-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.9. Esters of β-(3,5-dicyclohexyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.10. Amides of β-(3,5-di-tert-butyl-4-hydroxyphenyl)propionic acid e.g. N,N'-bis(3,5-di-tert-butyl-4-hydroxyphenylpropionyl)hexamethylene-diamine, N,N'-bis(3,5-di-tert-butyl-4-hydroxyphenylpropionyl)-trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-secbutyl-5'-tert-butyl, 4'-octoxy, 3',5'-di-tert-amyl and 3',5'-bis(α,α-dimethylbenzyl) derivatives.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example, 4-tert-butylphenyl salicylate, phenyl salicylate, octylphenyl salicylate, dibenzoylresorcinol, bis(4-tert-butylbenzoyl)-resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, e.g. of the methyl or ethyl ester, nickel complexes of ketoximes, e.g. of 2-hydroxy-4-methylphenyl undecyl ketoneoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the condensation product of 1-(2-hydroxyethyl)-2,2,6,6-tetramethyl-4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butanetetracarboxylate, 1,1'-(1,2-ethanediyl)bis(3,3,5,5-tetramethylpiperazinone).

2.7. Oxalic acid diamides, for example 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-disubstituted oxanilides and mixtures of o-and p-ethoxy-disubstituted oxanilides.

3. Metal deactivators, for example N,N'-diphenyloxalic acid diamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene) oxalodihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tertbutylphenyl) pentaerythritol diphosphite, tristearyl sorbitol triphosphite, tetrakis(2,4-di-tert-butylphenyl) 4,4'-biphenylene diphosphonite, 3,9-bis(2,4-di-tert-butylphenoxy)-2,4,8,10-tetraoxa-3,9-diphosphaspiro[5.5]undecane.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert.butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, optical brighteners, flameproofing agents, antistatic agents and blowing agents.

THE FOLLOWING EXAMPLES ILLUSTRATE THE EMBODIMENT OF THIS INVENTION.

EXAMPLE 1

6.21 g (0.055 mol) of chloroacetyl chloride dissolved in 30 ml of toluene are added slowly to a solution, cooled to −10° C., of 18.43 g (0.1 mol) of 4-ethylamino- 2,2,6,6-tetramethylpiperidine in 100 ml of toluene, while maintaining the above temperature.

After the end of the addition, the mixture is left for 2 hours at ambient temperature, a solution of 4.4 g (0.11 mol) of sodium hydroxide in 25 ml of water is added, and the mixture is then heated under reflux for 24 hours, with removal of the water previously added and the water of reaction. The reaction mixture is cooled to ambient temperature, filtered and evaporated in vacuo (24 mbar). The residue is taken up in n-hexane, from which the product of the formula

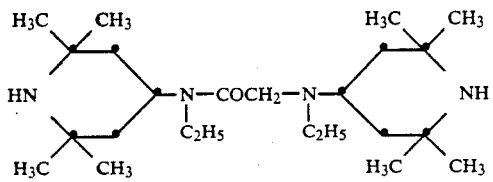

of melting point 96°–97° C. crystallizes.

Analysis for $C_{24}H_{48}N_4O$: Calculated: C 70.54%; H 11.84%; N 13.71% Found: C 70.47%; H 11.90%; N 13.78%

EXAMPLE 2

The same compound as in Example 1 is obtained by adding 29.02 g (0.2 mol) of an aqueous solution of 40% glyoxal to 73.72 g (0.4 mol) of 4-ethylamino-2,2,6,6-tetramethylpiperidine, while maintaining the temperature at 20°–25° C. The mixture is then heated at 40°–45° C. for 6 hours under reduced pressure (36 mbar), cooled to ambient temperature and treated with 150 ml of dichloromethane. The solution obtained is washed twice with 80 ml of water, dried over anhydrous $Na_2SO_4$ and evaporated in vacuo (100 mbar). The residue is taken up in hexane, from which the product of melting point 96°–97° C. crystallizes.

EXAMPLE 3

By a procedure analogous to that described in Example 1 with the appropriate reagents, the compound of the formula

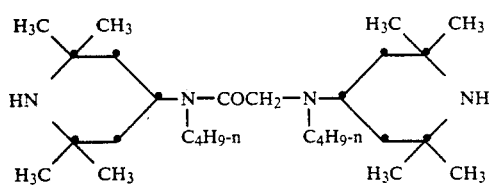

of melting point 83°–84° C. is prepared.

Analysis for $C_{28}H_{56}N_4O$: Calculated: C 72.36%; H 12.14%; N 12.06% Found: C 72.40%; H 12.15%; N 12.08%

EXAMPLE 4

52.1 g (0.2 mol) of N-(2-chloroacetyl)-N-(2,2,6,6-tetramethyl-4-piperidyl)-ethylamine (prepared as described in Example 15a of U.S. Pat. No. 4,618,634) and 41.46 g (0.3 mol) of finely ground anhydrous potassium carbonate are added to a solution of 15.63 g (0.1 mol) of 2,2,6,6-tetramethyl-4-piperidylamine in 160 ml of ethanol and the mixture is heated for 12 hours under reflux. The mixture is cooled to ambient temperature and filtered, and the solvent is removed in vacuo (24 mbar). The residue is dissolved in 200 ml of dichloromethane and the resulting solution is washed twice with water, dried over anhydrous sodium sulfate and evaporated to dryness in vacuo (100 mbar). The residue is taken up in n-octane, from which the product of the formula

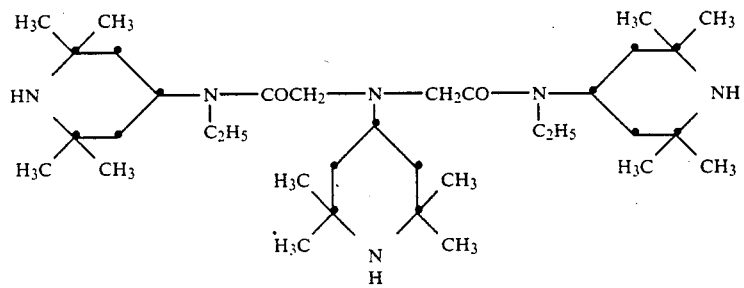

of melting point 155°–156° C. crystallizes.

Analysis for $C_{35}H_{68}N_6O_2$: Calculated: C 69.49%; H 11.33%; N 13.89% Found: C 69.60%; H 11.33%; N 13.89%

EXAMPLES 5–16

By a procedure analogous to that described in Example 4 and using the appropriate reagents, the following compounds of the formula

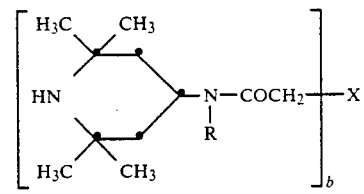

are prepared

| Example | R | b | X | Melting point (°C.) |
|---|---|---|---|---|
| 5 | —$C_2H_5$ | 2 | n-$C_4H_9$N⟨ | 106–107 |
| 6 | —$C_2H_5$ | 2 | n-$C_8H_{17}$N⟨ | 54–56 |
| 7 | —$C_2H_5$ | 2 | n-$C_{12}H_{25}$N⟨ | resin |

-continued

| Example | R | b | X | Melting point (°C.) |
|---|---|---|---|---|
| 8 | —C₂H₅ | 2 | [piperidine ring with H and N<] | 130–131 |
| 9 | —C₂H₅ | 2 | [C₆H₅CH₂N<] | 110–111 |
| 10 | —C₂H₅ | 2 | [—N⌒N—] piperazine | 191–192 |
| 11 | —C₄H₉-n | 2 | [piperidine ring with H and N<] | 122–124 |
| 12 | —C₄H₉-n | 2 | [tetramethylpiperidine with HN and N<] | 128–129 |
| 13 | —C₂H₅ | 4 | >N—(CH₂)₂—N< | 143–144 |
| 14 | —C₂H₅ | 4 | >N—(CH₂)₆—N< | 61–63 |
| 15 | —C₄H₉-n | 4 | >N—(CH₂)₂—N< | 115–116 |
| 16 | —C₄H₉-n | 4 | >N—(CH₂)₆—N< | 124–125 |

EXAMPLE 17

120.98 g (0.2 mol) of the product prepared in Example 4 are added slowly to a solution of 55.24 g (1.2 mol) of formic acid in 80 ml of water. The solution thus obtained is treated with 36.04 g (1.2 mol) of paraformaldehyde and heated under reflux for 8 hours. It is then cooled to ambient temperature and treated with 56 g (1.4 mol) of sodium hydroxide dissolved in 200 ml of water. The resulting precipitate is separated off by filtration, washed twice with water and dried at 100° C. in vacuo. This gives the product of the formula

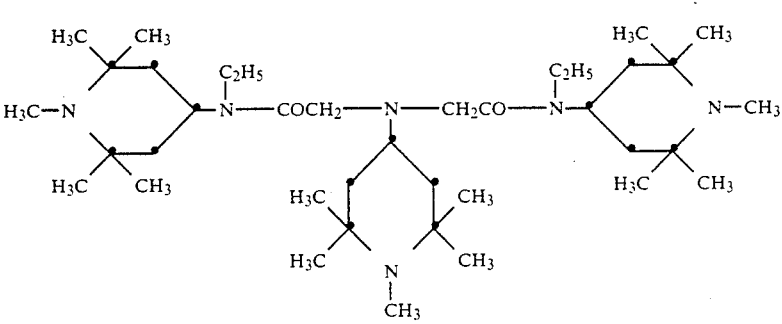

melting point 127°–128° C.

Analysis for $C_{38}H_{74}N_6O_2$: Calculated: C 70.54%; H 11.53%; N 12.99% Found: C 70.32%; H 11.60%; N 12.93%

EXAMPLE 18

The product described in Example 3 is treated analogously to Example 17, the product of the formula

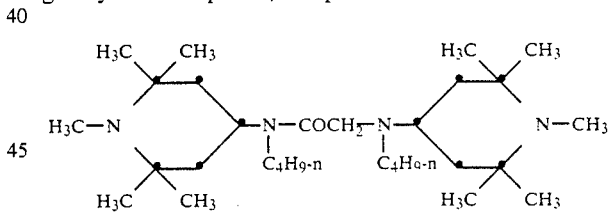

of melting point 90°–91° C. being obtained.

Analysis for $C_{30}H_{60}N_4O$: Calculated: C 73.11%; H 12.27%; N 11.37% Found: C 73.08%; H 12.25%; N 11.38%

EXAMPLE 19

36.3 g (0.3 mol) of allyl bromide are added to a solution of 46.48 g (0.1 mol) of the product described in Example 2 in 100 ml of 2-butanone and the mixture is heated at 70° C. for 2 hours. It is cooled to ambient temperature, treated with 44.22 g (0.32 mol) of finely ground anhydrous potassium carbonate and heated at 70° C. for a further 16 hours. After cooling to ambient temperature, the mixture is filtered and the solvent is removed in vacuo (24 mbar).

The residue is dissolved in 150 ml of dichloromethane and the solution is washed twice with water, dried over anhydrous sodium sulfate and evaporated to dryness in vacuo (100 mbar). The residue is taken up in 2-butanone, from which the product of the formula

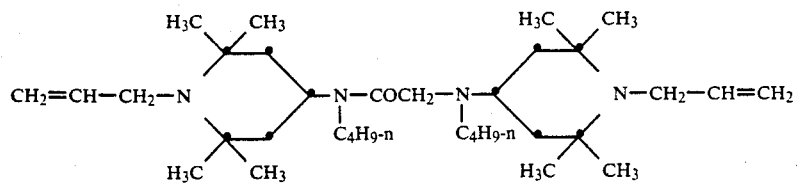

of melting point 73°–74° C. crystallizes.

Analysis for $C_{34}H_{64}N_4O$: Calculated: C 74.94%; H 11.84%; N 10.28% Found: C 75.01%; H 11.62%; N 10.30%

EXAMPLE 20

54.70 g (0.1 mol) of N,N'-bis-(2-chloroacetyl)-N,N'-bis(2,2,6,6-tetramethyl-4-piperidyl)-1,6-diaminohexane are added to a solution of 37.47 g (0.22 mol) of 4-methylamino-2,2,6,6-tetramethylpiperidine in 200 ml of 2-methoxyethanol and the mixture is heated under reflux for 7 hours.

After cooling to ambient temperature, 10 g (0.25 mol) of powdered sodium hydroxide are added and the mixture is stirred for 2 hours at ambient temperature and filtered, and the solvent is removed in vacuo (3 mbar).

The resulting residue is dissolved in n-hexane, from which the product of the formula of melting point 54°–55° C. crystallizes.

Analysis for $C_{48}H_{94}N_8O_2$: Calculated: C 70.71%; H 11.62%; N 13.74% Found: C 70.20%; H 11.56% N 13.74%

EXAMPLES 21–32

By a procedure analogous to that described in Example 20 and with the appropriate reagents, the following products of the formula

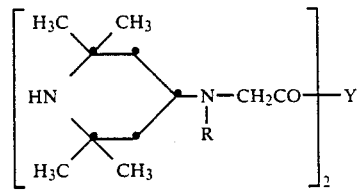

are prepared

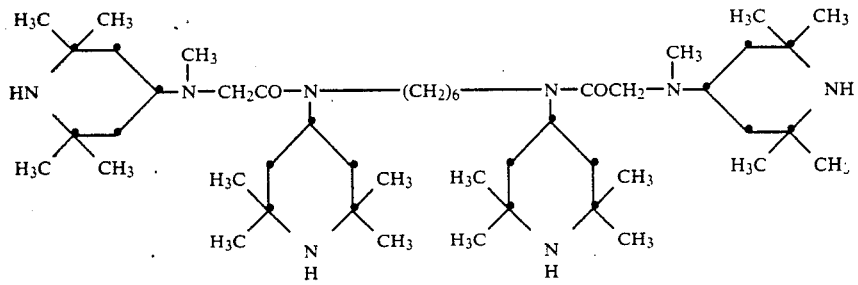

| Example | R | Y | Melting point (°C.) |
|---|---|---|---|
| 21 | —CH₃ | 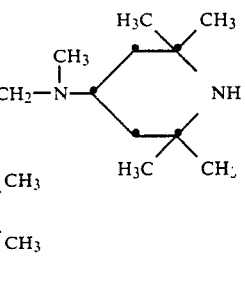 —N—(CH₂)₂—N— (each N bearing a 2,2,6,6-tetramethylpiperidin-4-yl group) | 221–223 |
| 22 | —CH₃ | —N⬡N— (piperazine) | 171–172 |
| 23 | —C₂H₅ | —N—(CH₂)₂—N— (each N bearing a 2,2,6,6-tetramethylpiperidin-4-yl group) | 248–249 |

-continued

| Example | R | Y | Melting point (°C.) |
|---|---|---|---|
| 24 | —C₂H₅ | [piperidine]—N—(CH₂)₃—N—[piperidine] (2,2,6,6-tetramethyl-4-piperidinyl groups) | 67–68 |
| 25 | —C₂H₅ | [piperidine]—N—(CH₂)₆—N—[piperidine] | 171–172 |
| 26 | —C₂H₅ | —N⟨⟩N— (diazacycle) | 127–128 |
| 27 | —C₄H₉-n | [piperidine]—N—(CH₂)₂—N—[piperidine] | 212–214 |
| 28 | —C₄H₉-n | [piperidine]—N—(CH₂)₃—N—[piperidine] | 95–96 |
| 29 | —C₄H₉-n | [piperidine]—N—(CH₂)₆—N—[piperidine] | 127–128 |
| 30 | —C₄H₉-n | —N—[2,2,6,6-tetramethylpiperidin-4-yl]—N(C₄H₉-n)— | 83–84 |
| 31 | —C₄H₉-n | —N⟨⟩N— | 177–178 |

-continued

| Example | R | Y | Melting point (°C.) |
|---|---|---|---|
| 32 | —C$_{12}$H$_{25}$-n | 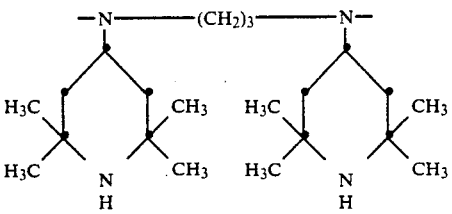 | resin |

EXAMPLE 33

1 g of each of the compounds indicated in Table 1, 0.5 g of tris-(2,4-di-t-butylphenyl) phosphite, 0.5 g of pentaerythritol tetrakis[(3,5-di-t-butyl-4-hydroxyphenyl)-propionate] and 1 g of calcium stearate are mixed in a slow mixer with 1,000 g of polypropylene powder of melt index=3 g/10 minutes (measured at 230° C. and 2.16 kg).

The mixtures are extruded at 200°-220° C. to give polymer granules which are then converted into stretched tapes of 50 μm thickness and 2.5 mm width, using a pilot type apparatus (Leonard-Sumirago (VA) Italy) under the following working conditions:
extruder temperature=210°-230° C.
head temperature=240°-260° C.
stretch ratio=1/6

The tapes thus prepared are exposed, mounted on a white card, in a model 65 WR Weather-O-Meter (ASTM G 26-77), with a black panel temperature of 63° C.

The residual tenacity is measured on samples, taken after various times of exposure to light, by means of a constant-speed tensometer; the exposure time in hours (T$_{50}$) needed to halve the initial tenacity is then calculated.

Tapes prepared under the same conditions as indicated above, but without the addition of stabilizers are exposed for comparison.

The results obtained are shown in Table 1.

TABLE 1

| Stabilizer | T$_{50}$ (hours) |
|---|---|
| without stabilizer | 380 |
| compound from Example 4 | 2450 |
| compound from Example 5 | 2250 |
| compound from Example 7 | 2240 |
| compound from Example 8 | 2280 |
| compound from Example 9 | 2300 |
| compound from Example 10 | 2160 |
| compound from Example 11 | 2020 |
| compound from Example 12 | 2060 |
| compound from Example 14 | 2030 |
| compound from Example 20 | 2440 |
| compound from Example 22 | 2280 |
| compound from Example 23 | 2840 |
| compound from Example 25 | 2870 |
| compound from Example 27 | 2200 |
| compound from Example 28 | 2770 |
| compound from Example 30 | 2530 |
| compound from Example 31 | 2240 |

What is claimed is:
1. A compound of the formula (I)

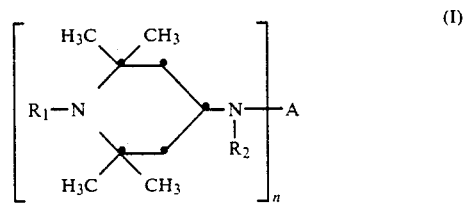

in which n is 1 or 2, R$_1$ is hydrogen, O·, OH, NO, CH$_2$CN, C$_1$-C$_8$-alkyl, allyl, benzyl, OH-monosubstituted C$_2$-C$_4$-alkyl, C$_1$-C$_{18}$-alkyloxy, C$_5$-C$_{12}$-cycloalkyloxy or C$_1$-C$_8$-acyl, R$_2$ is C$_1$-C$_{18}$-alkyl, C$_5$-C$_{12}$-cycloalkyl, C$_7$-C$_{12}$-phenylalkyl, C$_1$-C$_{12}$-alkoxy-monosubstituted C$_2$-C$_4$-alkyl, tetrahydrofurfuryl or a group of the formula (II)

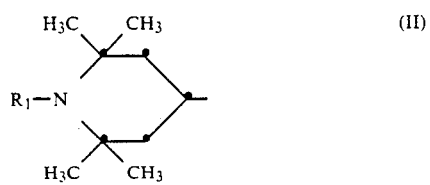

in which R$_1$ is as defined above, and, when n=1, A is a group of the formula (III)

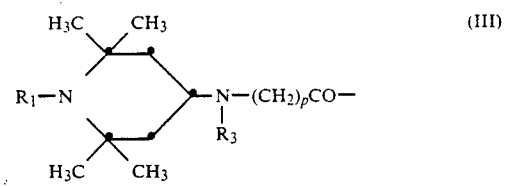

in which R$_1$ is as defined above, R$_3$ is as defined for R$_2$ and p is an integer from 1 to 5, or, when n=2, A is a group of the formula (IV), (V), (VI) or (VII)

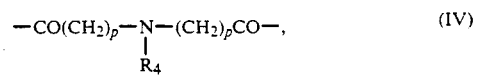

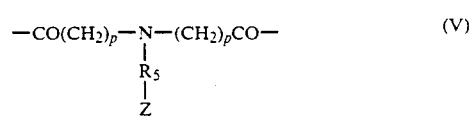

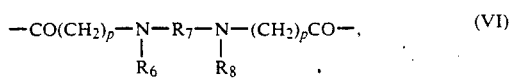

-continued $$-(CH_2)_pCO-\underset{R_6}{N}-R_7-\underset{R_8}{N}-CO(CH_2)_p- \quad (VII)$$

in which p is as defined above, $R_4$ is as defined above for $R_2$, $R_5$ is $C_2-C_{12}$-alkylene, $C_6-C_{15}$-cycloalkylene or xylylene, Z is a group of the formula (VIII)

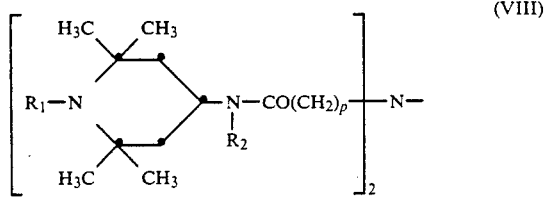

in which $R_1$, $R_2$ and p are as defined above, $R_6$ and $R_8$ which are identical or different are $C_1-C_8$-alkyl, cyclohexyl, benzyl or a group of the formula (II) and $R_7$ is $C_2-C_{12}$-alkylene, $C_6-C_{15}$-cycloalkylene or xylylene, or the group

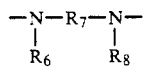

is a heterocyclic radical of the formula (IX) or (X)

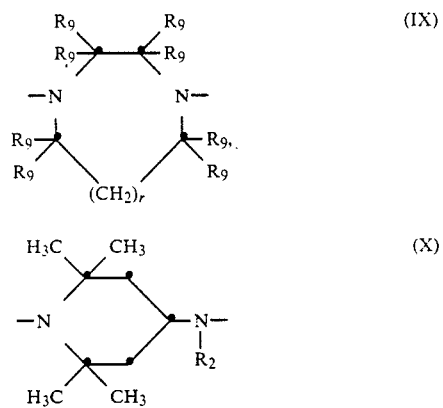

in which each $R_9$ independently is hydrogen or methyl, r is zero or 1 and $R_2$ is as defined above.

2. A compound of the formula (I) according to claim 1, in which n is 1 or 2, $R_1$ is hydrogen, $CH_2CN$, $C_1-C_4$-alkyl, allyl, benzyl, OH-monosubstituted $C_2-C_3$-alkyl or acetyl, $R_2$ is $C_1-C_{12}$-alkyl, $C_5-C_9$-cycloalkyl, benzyl, $C_1-C_8$-alkoxy-monosubstituted $C_2-C_3$-alkyl, tetrahydrofurfuryl or a group of the formula (II) and, when n=1, A is a group of the formula (III) in which $R_1$ is as defined above, $R_3$ is as defined for $R_2$ and p is an integer from 1 to 3, or, when n=2, A is one of the groups of the formulae (IV), (V), (VI) or (VII) in which p is as defined above, $R_4$ is as defined above for $R_2$, $R_5$ is $C_2-C_6$-alkylene or $C_6-C_{13}$-cycloalkylene, Z is a group of the formula (VIII) with $R_1$, $R_2$ and p being as defined above, $R_6$ and $R_8$ are a group of the formula (II) and $R_7$ is $C_2-C_6$-alkylene or $C_6-C_{13}$-cycloalkylene, or the group

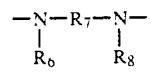

is 1,4-piperazinediyl or 5,5,7-trimethyl-1,4-homopiperazinediyl.

3. A compound of the formula (I) according to claim 1, in which n is 1 or 2, $R_2$ is $C_1-C_{12}$-alkyl, cyclohexyl, benzyl, $C_1-C_4$-alkoxy-monosubstituted $C_2-C_3$-alkyl or a group of the formula (II) and, when n=1, A is a group of the formula (III) with $R_1$ being as defined in claim 1, $R_3$ being as defined for $R_2$ and p being 1 or 2, or, when n=2, A is a group of the formula (IV), (V), (VI) or (VII) in which p is 1 or 2, $R_4$ is as defined above for $R_2$, $R_5$ is $C_2-C_6$-alkylene and Z is a group of the formula (VIII) with $R_1$ being as defined in claim 1, $R_2$ and p being as defined above, $R_6$ and $R_8$ are a group of the formula (II) and $R_7$ is $C_2-C_6$-alkylene, or the group

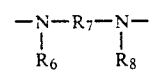

is a group of the formula (X) or 1,4-piperazinediyl.

4. A compound of the formula (I) according to claim 1, in which $R_1$ is hydrogen or methyl.

5. A compound of the formula (I) according to claim 1, in which n is 1 or 2, $R_1$ is hydrogen or methyl, $R_2$ is $C_1-C_{12}$-alkyl, cyclohexyl, benzyl, $C_1-C_4$-alkoxy-monosubstituted $C_2-C_3$-alkyl or a group of the formula (II) with $R_1$ being hydrogen or methyl and, when n=1, A is a group of the formula (III) with $R_1$ being hydrogen or methyl, $R_3$ being as defined above for $R_2$ and p being 1 or 2, or, when n=2, A is a group of the formula (IV), (V), (VI) or (VII) in which p is 1 or 2, $R_4$ is as defined above for $R_2$, $R_5$ is $C_2-C_6$-alkylene and Z is a group of the formula (VIII) with $R_1$, $R_2$ and p being as defined above, $R_6$ and $R_8$ are 2,2,6,6-tetramethyl-4-piperidyl or 1,2,2,6,6-pentamethyl-4-piperidyl and $R_7$ is $C_2-C_6$-alkylene, or the group

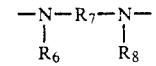

is 1,4-piperazinediyl.

6. A compound of the formula (I) according to claim 1, in which n is 1 or 2, $R_1$ is hydrogen or methyl, $R_2$ is $C_1-C_{12}$-alkyl and, when n=1, A is a group of the formula (III) in which $R_1$ is hydrogen or methyl, $R_3$ is $C_1-C_{12}$-alkyl and p is 1, or, when n=2, A is a group of the formula (IV), (V) or (VII) in which p is 1, $R_4$ is $C_1-C_{12}$-alkyl, cyclohexyl, benzyl, 2,2,6,6-tetramethyl-4-piperidyl or 1,2,2,6,6-pentamethyl-4-piperidyl, $R_5$ is $C_2-C_6$-alkylene, Z is a group of the formula (VIII) in which $R_1$ is hydrogen or methyl, $R_2$ is $C_1-C_{12}$-alkyl and p is 1, $R_6$ and $R_8$ are 2,2,6,6-tetramethyl-4-piperidyl or 1,2,2,6,6-pentamethyl-4-piperidyl and $R_7$ is $C_2-C_6$-alkylene, or the group

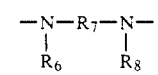

is 1,4-piperazinediyl.

7. A compound of the formula (I) according to claim 1, in which n is 2.

8. A compound of the formula (I) according to claim 1, in which n is 2, $R_1$ is hydrogen or methyl, $R_2$ is $C_1$-$C_8$-alkyl, A is a group of the formula (IV) or (VII) in which p is 1, $R_4$ is $C_4$-$C_{12}$-alkyl, cyclohexyl, benzyl, 2,2,6,6-tetramethyl-4-piperidyl or 1,2,2,6,6-pentamethyl-4-piperidyl, $R_6$ and $R_8$ are 2,2,6,6-tetramethyl-4-piperidyl or 1,2,2,6,6-pentamethyl-4-piperidyl and $R_7$ is $C_2$-$C_6$-alkylene or the group

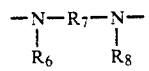

is 1,4-piperazinediyl.

9. A compound of the formula

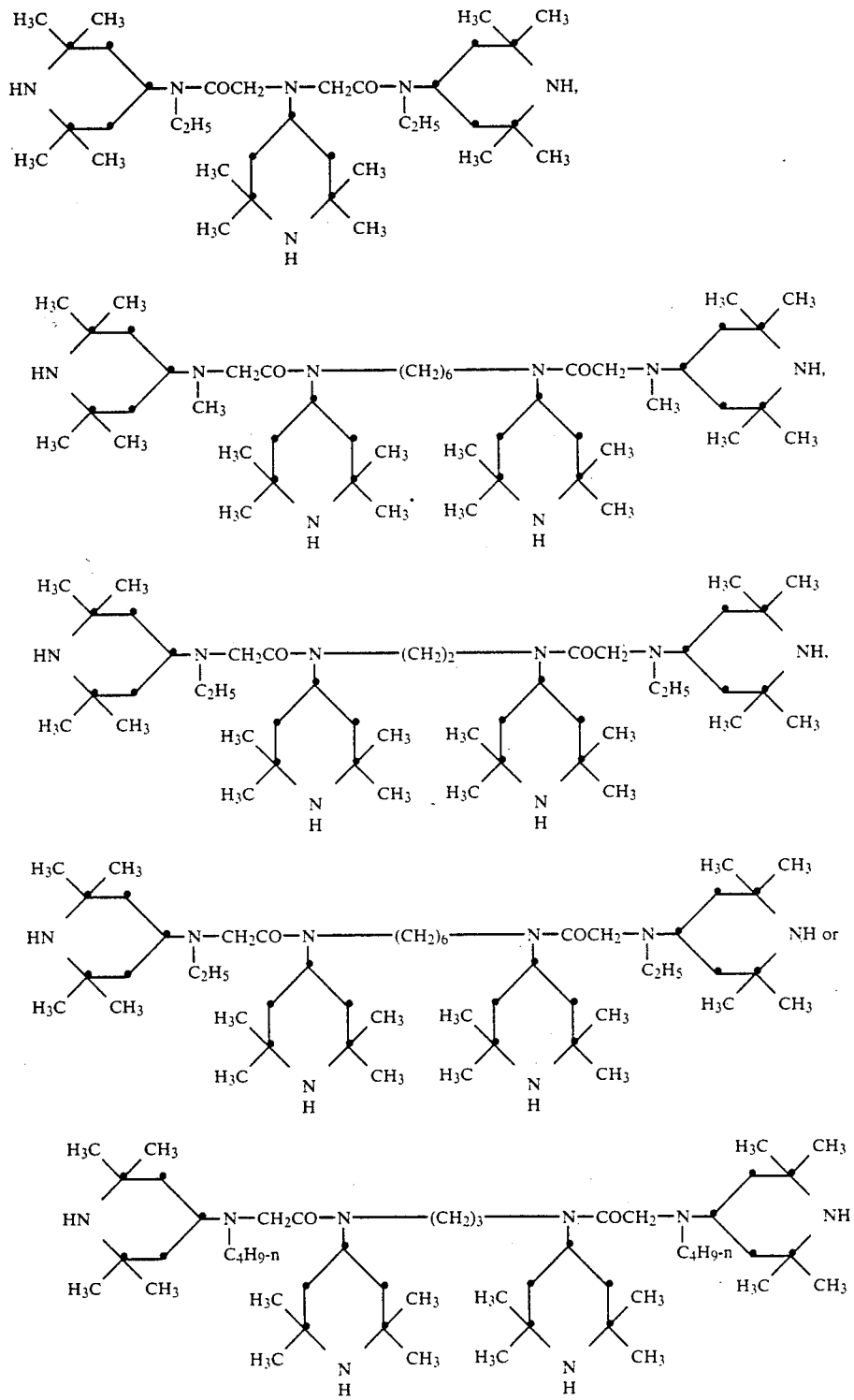

according to claim 1.

10. A composition comprising an organic material subject to thermal, oxidative or light-induced degradation and an effective stabilizing amount of a compound of the formula (I) according to claim 1.

11. A composition according to claim 10, wherein the organic material is a synthetic polymer.

12. A composition according to claim 11, which, in addition to the compound of the formula (I), also comprises other conventional additives for synthetic polymers.

13. A composition according to claim 10, wherein the organic material is a polyolefine.

14. A composition according to claim 10, wherein the organic material is polyethylene or polypropylene.

15. A method for stabilizing an organic material against thermal, oxidative or light-induced degradation, which comprises incorporating into the organic material an effective stabilizing amount of a compound of the formula (I) according to claim 1.

* * * * *